(12) United States Patent
Nam

(10) Patent No.: US 10,898,380 B2
(45) Date of Patent: Jan. 26, 2021

(54) ILLUMINATION CHOPPER

(71) Applicant: OCULIGHT CO., LTD., Gyeonggi-do (KR)

(72) Inventor: Dong Heun Nam, Seoul (KR)

(73) Assignee: OCULIGHT CO., LTD., Seongnam-si (KR)

( * ) Notice: Subject to any disclaimer, the term of this patent is extended or adjusted under 35 U.S.C. 154(b) by 185 days.

(21) Appl. No.: 14/901,131

(22) PCT Filed: Oct. 8, 2014

(86) PCT No.: PCT/KR2014/009466
§ 371 (c)(1),
(2) Date: Dec. 28, 2015

(87) PCT Pub. No.: WO2015/053550
PCT Pub. Date: Apr. 16, 2015

(65) Prior Publication Data
US 2016/0143782 A1 May 26, 2016

(30) Foreign Application Priority Data
Oct. 10, 2013 (KR) .................. 10-2013-0120806

(51) Int. Cl.
A61F 9/008 (2006.01)
A61F 9/007 (2006.01)
A61B 90/30 (2016.01)

(52) U.S. Cl.
CPC .......... *A61F 9/00825* (2013.01); *A61B 90/30* (2016.02); *A61F 9/007* (2013.01); *A61F 2009/0087* (2013.01); *A61F 2009/00887* (2013.01)

(58) Field of Classification Search
CPC ................. A61F 9/00825; A61F 9/007; A61F 2009/0087; A61F 2009/00887; A61F 9/0007; A61B 90/30
See application file for complete search history.

(56) References Cited

U.S. PATENT DOCUMENTS

| | | | | |
|---|---|---|---|---|
| 5,688,261 A | * | 11/1997 | Amirkhanian | A61B 18/22 606/13 |
| 5,951,543 A | * | 9/1999 | Brauer | A61B 18/201 606/10 |
| 6,428,553 B1 | * | 8/2002 | Trese | A61F 9/00736 606/16 |
| 6,592,541 B1 | * | 7/2003 | Kurwa | A61F 9/00745 604/22 |
| 2002/0151774 A1 | | 10/2002 | Soller et al. | |

(Continued)

FOREIGN PATENT DOCUMENTS

| | | |
|---|---|---|
| JP | 2003052624 A | 2/2003 |
| JP | 2005287887 A | 10/2005 |

(Continued)

*Primary Examiner* — Lynsey C Eiseman
*Assistant Examiner* — Jessandra F Hough
(74) *Attorney, Agent, or Firm* — Nelson Mullins Riley & Scarborough LLP; Kongsik Kim, Esq.

(57) ABSTRACT

The present invention provides an illumination chopper which allows a user to operate on the nucleus of a crystalline lens with a small piece while securing visibility through a chopper which is mounted at one end of an illuminator to form a predetermined angle with the illuminator.

4 Claims, 4 Drawing Sheets

(56) References Cited

U.S. PATENT DOCUMENTS

| | | | |
|---|---|---|---|
| 2006/0103835 A1* | 5/2006 | Artsyukhovich | A61F 9/007 356/73.1 |
| 2007/0179430 A1 | 8/2007 | Smith et al. | |
| 2008/0207992 A1 | 8/2008 | Scheller et al. | |
| 2010/0268203 A1 | 10/2010 | Smith | |
| 2013/0077048 A1* | 3/2013 | Mirlay | A61B 3/0008 351/206 |

FOREIGN PATENT DOCUMENTS

| | | |
|---|---|---|
| KR | 2001038045 Y1 | 3/1998 |
| KR | 20010038045 Y1 | 11/1998 |
| KR | 1020030010537 A | 5/2003 |

* cited by examiner

ILLUMINATION CHOPPER

TECHNICAL FIELD

The present invention relates to an illumination chopper, and more particularly to an illumination chopper in which a nucleus of a lens is operated into small pieces while visibility is secured through a chopper mounted on one end of an illuminator to form a predetermined angle with respect to an illuminator.

BACKGROUND ART

In the medical field, an illuminator is generally mainly used when retinal surgery is conducted, and a chopper is used when cataract surgery is conducted.

Here, an illuminator or a chopper is used separately according to the surgery, and in the process of the surgery, the operator conducts the surgery while gripping the illuminator or the chopper for surgery in one hand and gripping an illumination device or an auxiliary tool for securing the field of view in the other hand.

That is, because the operator conducts surgery while gripping surgery tools in both hands in the above-mentioned surgery method, excessive force is applied to the hands of the operator, causing pain and deteriorating the accuracy of the surgery as well when the surgery is conducted for a long time.

In addition, because an illumination device emits light to the diseased part of the patient from the outside, efficiency is degraded as compared with the emitted light.
(Patent Document 1) US2010-0268203 A1
(Patent Document 2) US2007-0179430 A1
(Patent Document 3) US2008-0207992 A1

DISCLOSURE

Technical Problem

Therefore, the present invention has been made in an effort to solve the above-mentioned problems, and provides an illumination chopper that separates the nucleus of a lens into small pieces while improving visibility through a coupling structure of a chopper that is mounted on one end of an illuminator in which an optical fiber is arranged at one end of the illuminator to form a predetermined angle with respect to the illuminator.

Technical Solution

In order to solve the above-mentioned problems, an illumination chopper according to the present invention includes: an illuminator that emits light; a chopper that is mounted on one end of the illuminator to form a predetermined angle with respect to the illuminator; and a grip part that surrounds the illuminator. Visibility is changed according to the predetermined angle formed by the illuminator and the chopper.

Preferably, the illuminator includes: a body having a body hole through which light passes; and an optical fiber that is situated inside the body, and which emits the light towards one end of the body.

Preferably, the illumination chopper includes: a power supply for supplying electric power to the optical fiber; and a power connection part that electrically connects the optical fiber and the power supply.

Preferably, when the predetermined angle is an acute angle, the light emitted from the illuminator illuminates a front side of the illuminator.

Preferably, when the predetermined angle is an obtuse angle, the light emitted from the illuminator is refracted by the chopper to illuminate a periphery of the chopper.

Advantageous Effects

As described above, according to the present invention, surgery that separates the nucleus of a lens into small pieces through a chopper while improving visibility by emitting light from the interior of an eyeball can be performed.

DESCRIPTION OF THE INVENTION

BEST MODE

Figure 1:
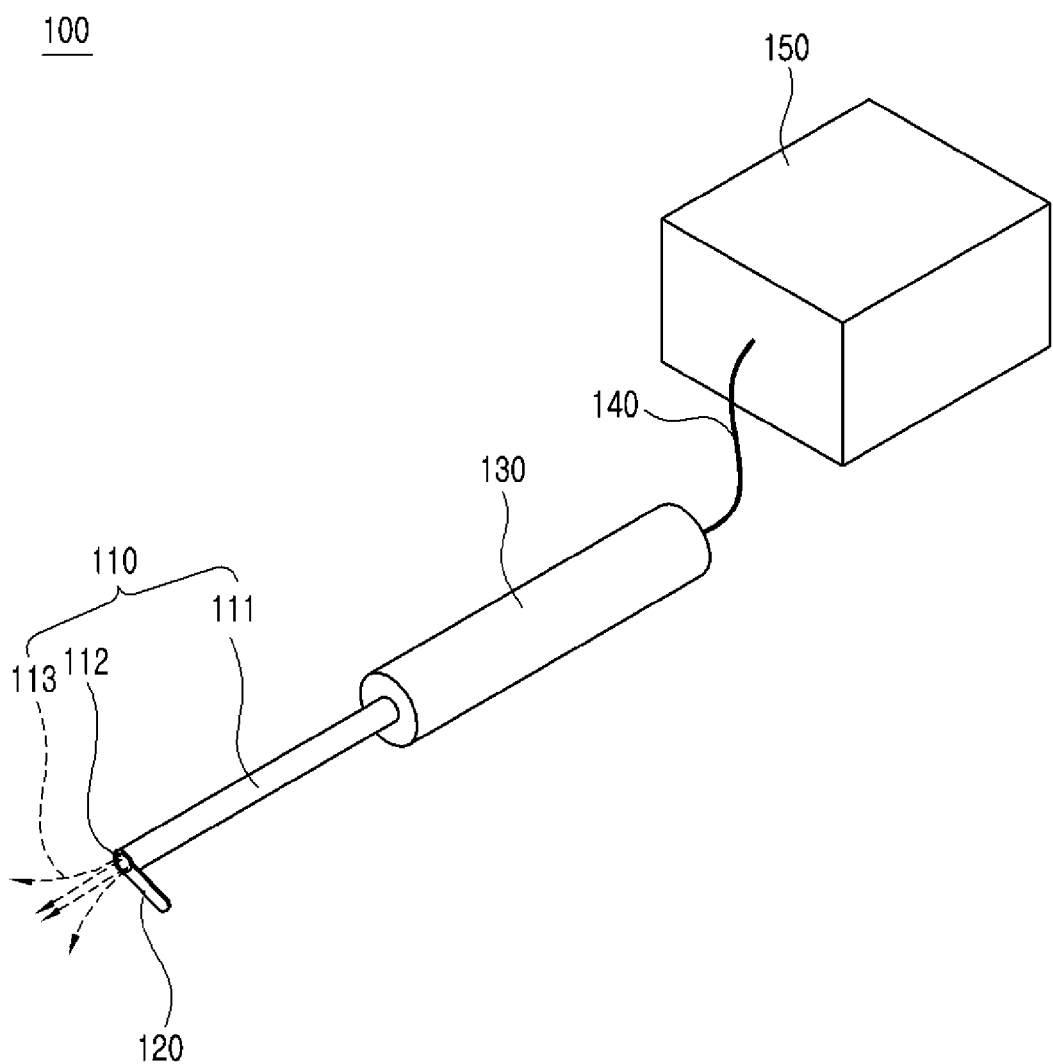
FIG. 1 is a perspective view from one side, which illustrates an illumination chopper according to a first embodiment of the present invention.

Elements of an illumination chopper according to the present invention may be used integrally or separately if necessary. Further, some elements may be omitted according to usage.

Preferred embodiments of the illumination chopper 100 according to the present invention will be described with reference to FIGS. 1 to 4. In the process, the thicknesses of the lines of the drawings or the sizes of the elements may be exaggerated for clarity and convenience of description. Further, the following terms are terms that are defined in consideration of their functions in the present invention, and may vary depending on an intention or customs of the user or the manager. Therefore, the definition of the terms should be made based on the overall contents of the specification.

First Embodiment

Hereinafter, an illumination chopper 100 according to a first embodiment of the present invention will be described with reference to FIGS. 1 and 2.

The illumination chopper 100 according to the first embodiment of the present invention includes an illuminator 110 that emits light, a chopper 120 that is mounted on one end of the illuminator 110 to form a predetermined angle with the illuminator 110, a grip part 130 that surrounds the illuminator 110, a power supply 140 that is electrically connected the illuminator 110, and a power connection part 150 that electrically connects the illuminator 110 and the power supply 140.

The illuminator 110 includes a body 111, a body hole 112, and optical fibers 113.

The body 111 is a kind of a tool that is generally used when cataract surgery is conducted, and has the form of a hollow tube. The body 111 includes the body hole 112 through which light passes, and a plurality of optical fibers 113 for emitting light to the outside are situated in the interior of the body 111.

The body hole 112 is a hole situated inside the body 111, and the plurality of optical fibers 113 are situated in the body hole 112.

The optical fibers 113 are situated in the interior of the body 111, and light is emitted towards one end of the body 111.

The chopper 120 is mounted on one end of the illuminator 110 and is arranged to form a predetermined angle with the illuminator 110.

Figure 2:
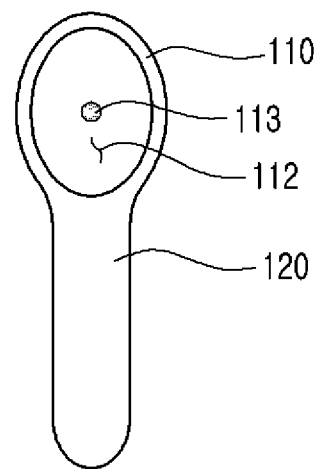
FIG. 2 is a front view from one side, which illustrates the illuminator of FIG. 1.

In more detail, as illustrated in FIG. 1, the chopper 120 may be arranged so as not to block light emitted from the optical fibers 113.

That is, in the first embodiment of the present invention, the predetermined angle is an acute angle, and the light emitted from the illuminator 110 illuminates the front side of the illuminator 110.

The coupling structure allows the operator to emit light into an eyeball by using the illuminator 110 to improve visibility, and to conduct cataract surgery with the chopper 120 at the same time.

It is preferable that the grip part 130 is formed to surround the illuminator 110 and is formed of a resilient material. The grip part 130 helps the operator conduct cataract surgery or the like while the operator grips the grip part 130 with one hand thereof.

The power supply 140 is a unit for supplying electric power to the optical fibers 113, and is electrically connected to the power connection part 150. The power supply 140 may be any unit that can supply electric power.

The power connection part 150 is an electric wire that electrically connects the optical fibers 113 and the power supply 140.

Second Embodiment

Hereinafter, an illumination chopper 100' according to a second embodiment of the present invention will be described with reference to FIGS. 3 and 4, in which all the elements except for the chopper 120' are the same as those of the first embodiment and will be described with reference to the second embodiment of the present invention.

The illumination chopper 100' according to the second embodiment of the present invention includes an illuminator 110' that emits light, a chopper 120' that is mounted on one end of the illuminator 110' to form a predetermined angle with respect to the illuminator 110', a grip part 130' that surrounds the illuminator 110', a power supply 140' that is electrically connected the illuminator 110', and a power connection part 150' that electrically connects the illuminator 110' and the power supply 140'.

The chopper 120' is mounted on one end of the illuminator 110' and is arranged to form a predetermined angle with respect to the illuminator 110'.

That is, in the second embodiment of the present invention, the predetermined angle is an obtuse angle, and the light emitted from the illuminator 110' is refracted by the chopper 120' to illuminate a periphery of the chopper 120'.

Figure 3:
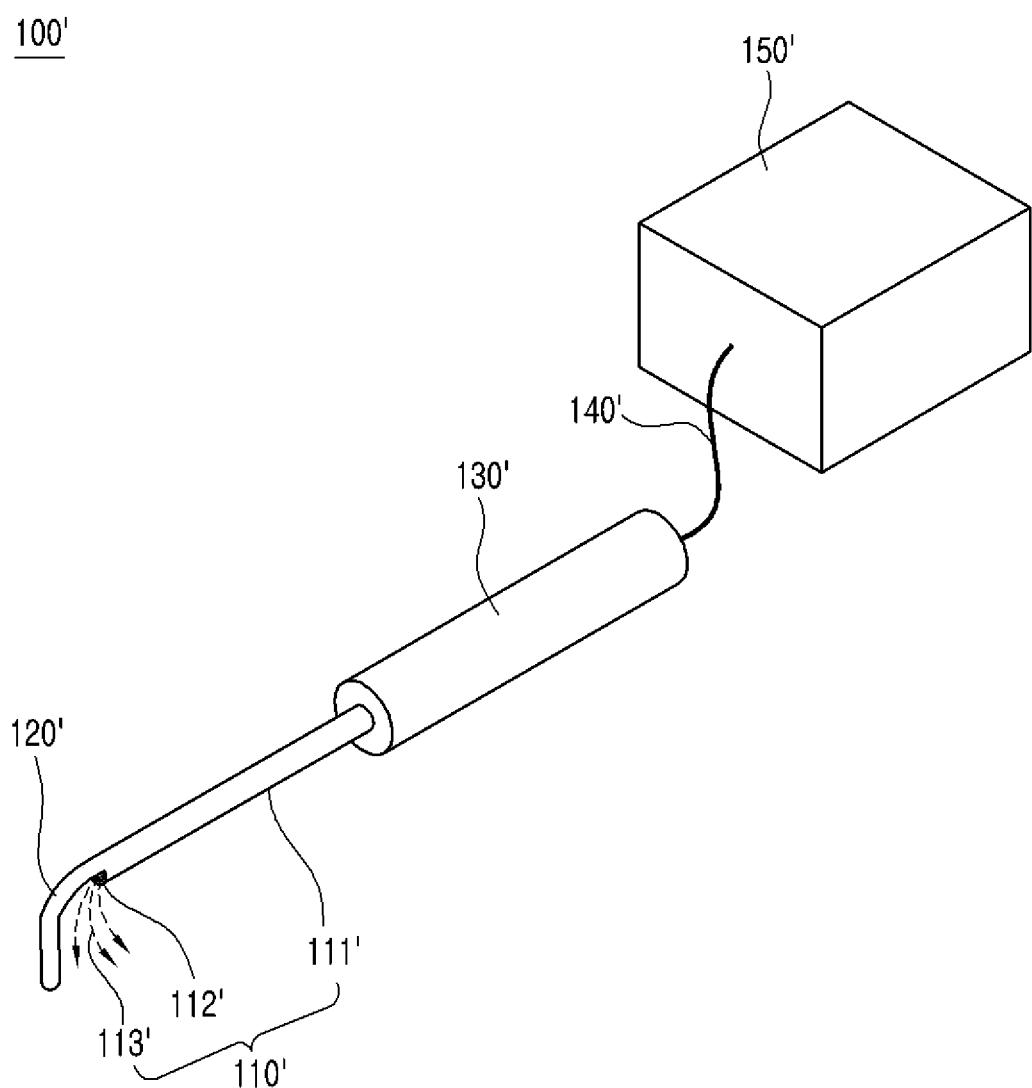
FIG. 3 is a perspective view from one side, which illustrates an illumination chopper according to a second embodiment of the present invention.
Figure 4:
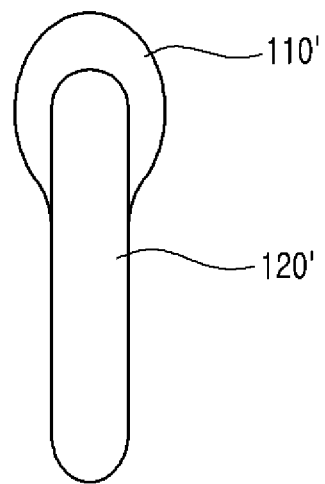
FIG. 4 is a front view from one side, which illustrates the illuminator of FIG. 3.

In more detail, as illustrated in FIG. 3, the chopper 120' is configured such that the light emitted from the optical fibers 113' is refracted by the chopper 120' so that the field of view around the chopper 120' is secured.

The coupling structure allows the operator to emit light into an eyeball by using the illuminator 110' to improve visibility, and to conduct cataract surgery with the chopper 120' at the same time.

Here, the choppers 120 and 120' according to the first and second embodiments of the present invention are somewhat different in the coupling relationships with the illuminators 110 and 110', and it is apparent that the structure may be fixed after being variably adjusted to provide the operator with convenience during cataract surgery.

Although the present invention has been described with reference to the preferred embodiments of the present invention, it will be understood that the present invention may be variously corrected and modified by those skilled in the art to which the present invention pertains without departing from the spirit and area described in the claims.

The invention claimed is:

1. An illumination chopper comprising:
   an illuminator having an optical fiber for emitting light from interior of an anterior segment of an eyeball which includes a cornea, an iris, and a crystalline lens, the illuminator being configured to illuminate the interior of the anterior segment of the eyeball and to improve visibility in the interior of the anterior segment of the eyeball, the illuminator comprising a body having first and second ends and a body hole extending through the body to the second end in which the optical fiber is fixedly disposed such that light emitted by the optical fiber passes through the second end of the body;
   a chopper being fixedly mounted to form a predetermined angle with respect to the illuminator on a top side of the body on the second end, wherein the chopper includes a first portion that extends away from the top side of the body and a second portion that curves downward from the first portion and away from the top side of the body so that the second portion of the chopper is disposed in front of, and spaced a distance from, the second end of the body whereby the chopper refracts light emitted from the optical fiber after the emitted light passes through the second end of the body and the emitted light illuminates the interior of the anterior segment of the eyeball around a periphery of the chopper; and
   a grip part that surrounds the body;
   wherein the illuminator of the illumination chopper provides illumination to the interior of the anterior segment of the eyeball at the same time as surgery is performed by the chopper of the illumination chopper, and
   wherein the second portion of the chopper is extended downward substantially below a bottom side of the second end of the body, which is opposite from the top side of the second end of the body, enabling the chopper to chop a nucleus of the crystalline lens into small pieces during cataract surgery.

2. The illumination chopper according to claim 1, wherein the illumination chopper comprises:
   a power supply for supplying electric power to the optical fiber; and
   a power connection part that electrically connects the optical fiber and the power supply.

3. The illumination chopper according to claim 1, wherein the chopper and the illuminator are integrally formed.

4. The illumination chopper according to claim 1, wherein the chopper has a rounded and blunt distal tip.

* * * * *